United States Patent
Beck et al.

(10) Patent No.: US 7,620,233 B2
(45) Date of Patent: Nov. 17, 2009

(54) PROCESS FOR CHECKING A LASER WELD SEAM

(75) Inventors: Markus Beck, Elchingen (DE); Thomas Herzinger, Ulm (DE)

(73) Assignee: Daimler AG, Stuttgart (DE)

( * ) Notice: Subject to any disclaimer, the term of this patent is extended or adjusted under 35 U.S.C. 154(b) by 588 days.

(21) Appl. No.: 11/031,858

(22) Filed: Jan. 7, 2005

(65) Prior Publication Data

US 2005/0163364 A1 Jul. 28, 2005

(30) Foreign Application Priority Data

Jan. 7, 2004 (DE) .................... 10 2004 001 169
Apr. 5, 2004 (DE) .................... 10 2004 016 669

(51) Int. Cl.
*G06K 9/00* (2006.01)

(52) U.S. Cl. ............. 382/152; 219/121.13; 219/121.63; 219/121.83; 382/149; 700/166

(58) Field of Classification Search ............. 219/121.6, 219/121.63, 121.64, 121.76, 121.83, 121.82, 219/121.13, 121.61, 121.78; 250/559.01, 250/559.05, 559.29; 382/143, 152, 141, 382/149; 700/166
See application file for complete search history.

(56) References Cited

U.S. PATENT DOCUMENTS

| 4,328,416 | A | * | 5/1982 | Dudley et al. ................. 250/202 |
| 4,477,713 | A | * | 10/1984 | Cook et al. ............. 219/124.34 |
| 4,491,718 | A | * | 1/1985 | Cook et al. ............. 219/124.22 |
| 4,501,950 | A | * | 2/1985 | Richardson ............. 219/124.34 |
| 4,924,063 | A | * | 5/1990 | Buchel et al. ........... 219/121.64 |
| 5,150,175 | A | * | 9/1992 | Whitman et al. ............. 356/429 |
| 5,329,091 | A | * | 7/1994 | Bissinger ............... 219/121.63 |
| 5,572,102 | A | * | 11/1996 | Goodfellow et al. ... 318/568.13 |
| 6,261,701 | B1 | * | 7/2001 | Fields, Jr. .................... 428/577 |
| 6,311,099 | B1 | * | 10/2001 | Jasper et al. ................. 700/166 |
| 6,399,915 | B1 | * | 6/2002 | Mori et al. ............. 219/121.83 |
| 6,452,131 | B2 | * | 9/2002 | Britnell ................... 219/121.6 |
| 6,479,786 | B1 | * | 11/2002 | Fields et al. ........... 219/121.63 |
| 6,621,047 | B2 | * | 9/2003 | Kessler et al. .......... 219/121.83 |
| 6,998,569 | B2 | * | 2/2006 | Schumacher ........... 219/121.63 |
| 7,081,599 | B2 | * | 7/2006 | Aebersold ............. 219/121.63 |
| 7,107,118 | B2 | * | 9/2006 | Orozco et al. ............... 700/166 |
| 2004/0114662 | A1 | | 6/2004 | Mesler |
| 2004/0134891 | A1 | * | 7/2004 | Schumacher ........... 219/121.63 |
| 2005/0163364 | A1 | * | 7/2005 | Beck et al. ................... 382/152 |

FOREIGN PATENT DOCUMENTS

| DE | 43 11 320 A1 | 10/1994 |
| DE | 100 13 892 A1 | 12/2000 |
| DE | 101 58 095 A1 | 6/2003 |

* cited by examiner

*Primary Examiner*—Gregory M Desire
(74) *Attorney, Agent, or Firm*—Patent Central LLC; Stephan A. Pendorf

(57) ABSTRACT

When laser beam welding one or more work pieces faults may occur, which lead to unacceptable losses in quality. A check process is provided, which reliably recognizes seam faults in a seam which is introduced into one or more workpieces by means of laser beam welding. Characteristic signals are detected from the region of the seam using a sensor and compared with an index value or set value, and only signals are taken into consideration which are detected in a characteristic time interval following the laser beam welding, which begins, at the earliest, following the solidification of the seam.

17 Claims, No Drawings

PROCESS FOR CHECKING A LASER WELD SEAM

BACKGROUND OF THE INVENTION

1. Field of the Invention

The invention concerns a process for checking a laser weld seam.

2. Related Art of the Invention

When laser beam welding one or more work pieces faults may occur, which lead to unacceptable losses in quality. For quality assurance, both subjective visual inspections as well as automated checks of the seam are the norm.

In the automated processes the work site is conventionally monitored during welding using point or surface detectors (cameras). This type of process can not detect faults which do not occur until after the actual interaction of laser beam and work piece, in particular, solidification phenomena. Beyond this, certain irregularities relevant to quality are not recognized, since relevant process signals are overridden by stronger signals of the process illumination with no information value.

This problem is partially compensated for by a process according to DE 43 21 463 C2. There the melt pool or melt flow side of the seam is monitored by a following IR-detector, so that the overriding of the quality-relevant signals by the interfering signals of the process light are reduced, however not excluded.

SUMMARY OF THE INVENTION

It is the task of the present invention to provide a check process, which reliably recognizes seam faults.

This problem is partially compensated for by a process according to DE 43 21 463 C2 (U.S. Pat. No. 5,283,416; U.S. Pat. No. 5,360,960). There the melt pool or melt flow side of the seam is monitored by a following IR-detector, so that the overriding of the quality-relevant signals by the interfering signals of the process light are reduced, however not excluded.

DETAILED DESCRIPTION OF THE INVENTION

In accordance with the invention, for checking of the seam which is introduced into one or more workpieces by means of laser beam welding, characteristic signals are detected from the region of the seam using a sensor and compared with an index value or set value, wherein only signals are taken into consideration which are detected in a characteristic time interval following the laser beam welding, which begins, at the earliest, following the solidification of the seam.

In comparison to the processes according to the state of the art, which examine the process luminescence during laser beam welding, the checking in accordance with the invention occurs exclusively on the basis of signals which are received or detected after laser beam welding. In contrast to the process according to DE 43 21 463 C2, the inventive checking occurs exclusively on the basis of signals, which are received or detected, at the earliest, after the solidification of the seam.

Thereby seam faults or defects are detected substantially more reliably, since during, and also just shortly after extinguishing of the process illumination, parts of the workpiece material are still in molten liquid phase. Various physical phenomenon, in particular minimizing of the boundary surface energy, however, also convection and diffusion, can bring about that the molten liquid phase changes its outer surface shape as well as its inner structure and therewith the seam quality during the solidification.

In comparison to the processes according to the state of the art, which examine the process luminescence during laser beam welding, the checking in accordance with the invention occurs exclusively on the basis of signals which are received or detected after laser beam welding. In contrast to the process according to DE 43 21 463 C2 (U.S. Pat. No. 5,283,416; U.S. Pat. No. 5,360,960), the inventive checking occurs exclusively on the basis of signals, which are received or detected, at the earliest, after the solidification of the seam.

The comparison of the inventive signals with the desired values can occur by known processes, for example according to DE 43 21 463 C2.

Thus, in accordance with a preferred embodiment, the characteristic time interval is defined depending upon the material characteristics of the workpiece and depending upon process parameters of the laser processing. Therein respectively various time points can be selected for beginning and ending the measurement time: the absolute earliest useful point in time for beginning is the time at which at least a thin skin of the weld seam has solidified, preferred is the solidification of the total material which had been molten, it is however also conceivable to wait for a short time interval after this period. The earliest point in time for the end of the time interval is determined by the minimal length of the time interval which is necessary in order to receive a sufficient amount of signal data. For increasing the measurement quality, the time interval can however be selected to be longer.

The comparison of the inventive signals with the desired values can occur by known processes, for example according to DE 43 21 463 C2 (U.S. Pat. No. 5,283,416; U.S. Pat. No. 5,360,960).

In one preferred embodiment of the invention signals of optical and/or thermal type are received, which are emitted or reflected out of the area of the seam. The advantage of this design or arrangement is comprised therein, that from this type of data it becomes possible in particularly simple manner according to known processes to detect seam defects.

Particularly advantageous is the use of a CCD-camera for receiving the signals. This type of camera is useable in the optical and thermal (IR) realm and provides with minimal manipulative complexity a much greater wealth of data in comparison to optical or thermal point sensors. However, also other electronic cameras are suited, for example a CMOS-camera. For less stringent requirements point sensors such as diodes may also suffice.

In a further preferred embodiment of the invention a measurement signal of the optical and/or thermal type is emitted towards the direction of the area of the seam during the above defined time interval, and then the signal reflected from the seam is detected. The measurement signal can be emitted during the entire duration of the measurement time interval or also continuously, however a short measuring impulse is sufficient so long as it occurs during the measurement interval. Thereby one is no longer restricted to the reception of signals which result from the energy which has been input by the preceding laser impulse, that is, optical and/or thermal emission of the already hardened however still glowing, then still hot, and finally warm, seam.

The measurement signal can be emitted by the welding laser or another emitter. What is important is that the energy input into the seam remains so small, that the material is not caused to remelt.

It has been found to be particularly advantageous to use a scanner device in order to steer the laser beam on the surface of the workpiece to be welded. A scanner device is a particularly rapid and flexible beam deflecting device, for example a mirror system (comprised of at least one single-axis or multi-axis controllable pivotable mirror) or also of acousto-optical modulators.

The great advantage of this embodiment of the inventive process is comprised in the high speed, which with the scanner device can guide or steer the laser beam with high precision over the surface of a workpiece. Thereby the same laser beam (with the same output and focusing, however, with different speeds of advance) can be guided over the exact same seam in very short time frame both for welding of a predetermined seam as well as for use as a measurement signal.

The design of the sensor is basically any, so long as it is capable of receiving only the characteristic signals from the area of the seam. As particularly advantageous it has been found to use the already present beam guidance of the scanner device. For this, essentially one beam splitter and optionally one shutter is inserted in the beam path of the laser beam. The beam splitter directs the measurement signal to the reflection path from the surface of the workpiece toward the sensor. The shutter is provided between beam splitter and sensor and closes this path during welding, in order to protect the sensor from too strong a signal.

This physical design makes it possible to use the same laser both as the processing tool as well as the measurement instrument. The scanner device enables the workpiece and/or processing lenses, during processing and measuring, to be moved already in the direction towards other processing locations and thereby minimizes the process time.

In the following the inventive process will be described in greater detail on the basis of an illustrative embodiment:

According to the illustrative embodiment first a suitable characteristic time interval for a given workpiece and given laser parameters is determined empirically. For this, first a bit of workpiece material is melted and thereafter is observed during the transition from the molten liquid to solid phase using an IR-CCD-camera, in order to determine characteristic IR signals for the phase transition. Thereafter, a continuous observation of the laser seam occurs using this IR-CCD-camera. At a point in time at which a relative equilibrium has already been established between energy input by the welding laser beam and energy dissipation via thermal conductors through the seam wall and air has established itself, the time sequence of the seam cooling directly following the end of a welding process begins to be observed. This observation is repeated multiple times and each time the point in time is determined, at which the characteristic signal of the phase transition is arrived at significant locations of the seam. These times are averaged. The average value provides a time-tested and proven value for the earliest start of the characteristic time interval for the total time of the laser processing, since it is presumed, that the cooling at the beginning of the seam occurs more rapidly, that is, prior to reaching the relative equilibrium, on the basis of the still-cold seam environment. As the length of the characteristic time interval, the two-fold of the minimal necessary measurement duration is selected. The minimal necessary measurement duration is just sufficient, in order to detect a significant signal.

After a suitable characteristic time interval is defined, the actual processing (fabrication or manufacture) can occur. According to this illustrative embodiment two plate-shaped workpieces with short seams (in the manner of a step-seam) are welded to each other. In order to minimize the process time, after completion of a step seam, it is not waited until the above defined earliest begin of the characteristic time interval and then measured, but rather first a second step seam is welded. After completion of the second weld the earliest begin of the characteristic time interval of the preceding seam is already reached or exceeded and the seam solidifies. The scanner device now guides the same laser beam, but with increased rate of advance, as measurement signal over the preceding seam. On the basis of the increased rate of advance the seam is not remolten, but rather only warmed. The IR-radiation emitted from the seam is guided from a beam splitter in the beam path of the laser beam to the IR-CCD-camera and there is detected. Thereafter first a further seam is welded, before the second seam is checked, in order there also to wait for its solidification.

The IR-signals of the IR-CCD-camera, which were detected during the characteristic time interval respectively following the laser processing, are compared with the previously established expected values. The comparison occurs by known processes from the state of the art, for example according to DE 43 21 463 C2.

The inventive process proves itself, in the embodiment of the above described example, as particularly suited for a rapid and simple checking of the laser weld seam of body panels or sheet metal as used in the automobile industry, since there particularly high quality requirements exist, which cannot be achieved sufficiently satisfactorily with the processes according to the existing state of the art.

The IR-signals of the IR-CCD-camera, which were detected during the characteristic time interval respectively following the laser processing, are compared with the previously established expected values. The comparison occurs by known processes from the state of the art, for example according to DE 43 21 463 C2 (U.S. Pat. No. 5,283,416; U.S. Pat. No. 5,360,960). For example, while U.S. Pat. No. 5,360,960 teaches a method for monitoring a laser process wherein energy from a laser source is delivered to a workpiece along a process path while producing light emitting plasma at a beam delivery point along said path, and comprising the steps of: (a) positioning a light detecting means so that said detecting means receives light from said plasma and provides a light signal having a value which varies with changes in the intensity of the received light over a predetermined test interval; (b) providing a plurality of limits with each limit having a different value: (c) providing a predetermined plurality of light samples of said light signal over a predetermined test interval; (d) comparing each said light sample with each of said limits and providing a violation indication each time a light sample violates one of said limits; (e) counting the number of violation indications for each limit during the predetermined test interval; (f) evaluating the laser process as a function of the number of violation indications; and (g) providing an output indication of the evaluation, the present invention in contrast does not receive light from the plasma, but instead, involves (a) determining the time after welding at which at least a thin skin has solidified on the weld seam and setting this as the earliest measurement start time for a characteristic interval, (b) selecting an optical or thermal signal to be emitted onto and reflected from the weld seam during said characteristic interval, (c) determining the minimal length of a time interval necessary in order to receive detectable signal data, and setting this as the minimal duration of the characteristic time interval, (d) laser welding the materials to form a weld seam, (e) emitting the optical or thermal signal onto the seam in said area in which at least a thin skin has solidified and detecting reflected signal data, (e) comparing the detected reflected signal data with desired values, (f) providing a violation signal each time the detected reflected signal data does not correspond with the desired values, and (g) evaluating the laser weld seam on the basis of said violation signals, wherein only signals detected within the characteristic time interval are taken into consideration.

Finally, for a series of applications for which the quality requirements are somewhat less stringent, measurements would also suffice using optical and/or thermal point sensors in place of a CCD-camera or CMOS-camera.

The invention claimed is:

1. A process for checking a laser weld seam, comprising:
    selecting materials to be welded and the process parameters of the laser welding process for forming a weld seam,
    determining the time after welding at which at least a thin skin has solidified on the weld seam and setting this as the earliest measurement start time for a characteristic interval,
    selecting an optical or thermal signal to be emitted onto and reflected from the weld seam during said characteristic interval,
    determining the minimal length of a time interval necessary in order to receive detectable signal data, and setting this as the minimal duration of the characteristic time interval,
    laser welding said materials to form a weld seam by a computer controlled process comprising:
    emitting said optical or thermal signal onto said seam in said area in which at least a thin skin has solidified and detecting reflected signal data,
    comparing the detected reflected signal data with desired values,
    providing a violation signal each time the detected reflected signal data does not correspond with the desired values, and
    evaluating the laser weld seam on the basis of said violation signals,
    wherein only signals detected within the characteristic time interval are taken into consideration.

2. The process according to claim 1, wherein the characteristic time interval is defined depending upon the material characteristics of the workpiece and the process parameters of the laser beam.

3. The process according to claim 1, wherein detected signals of the optical and/or thermal type are emitted or reflected out from the area of the seam.

4. The process according to claim 1, wherein the signals are detected using a CCD-camera or a CMOS-camera.

5. The process according to claim 1, wherein the measurement signal is produced by redirecting the welding laser back onto the already welded seam with sufficient energy to produce a reflected signal but without causing the seam to remelt, and is directed in the direction of and onto the seam via suitable beam deflection mechanisms.

6. The process according to claim 5, wherein the measurement signal is produced by the welding laser and is directed in the direction of and onto the seam via a scanner device.

7. The process according to claim 1, further comprising placing a beam splitter in the beam path of the laser beam, such that the beam splitter directs the measurement signal to the weld seam in said area in which the weld seam has solidified, and such that the reflection of the laser from the area in which the weld seam has solidified is directed to the sensor.

8. The process according to claim 7, further comprising placing a shutter in the beam path of the laser beam, wherein said shutter is provided between beam splitter and sensor and closes this path during welding, in order to protect the sensor from too strong a signal.

9. The process according to claim 1, wherein the earliest measurement start time for the characteristic interval is the time at which the weld seam completely solidifies.

10. The process according to claim 1, wherein the two-fold of the minimal necessary measurement duration in order to receive detectable signal data is set as the minimal duration of the characteristic time interval.

11. The process according to claim 1, wherein said material is metal.

12. The process according to claim 11, wherein said metal is in the form of sheet metal.

13. A process for checking a laser weld seam, comprising:
    selecting materials to be welded and the process parameters of the laser welding process for forming a weld seam,
    determining the time after welding at which said weld seam has solidified and setting this as the earliest measurement start time for a characteristic interval,
    selecting a speed or power at which said laser when redirected onto said solidified weld seam does not cause said weld seam to remelt,
    determining the minimal length of a time interval necessary in order to receive a detectable signal data from the reflection of said redirected laser beam, and setting the two-fold of this as the minimal duration of the characteristic time interval,
    laser welding said materials to form a weld seam by a computer controlled process comprising:
    redirecting said laser beam onto said seam in said area in which said weld seam has solidified and detecting reflected signal data,
    comparing the detected reflected signal data with desired values,
    providing a violation signal each time the detected reflected signal data does not correspond with the desired values, and
    evaluating the laser weld seam on the basis of said violation signals,
    wherein only signals detected within the characteristic time interval are taken into consideration.

14. A computer controlled process for checking a laser weld seam, wherein said computer directs process steps comprising:
    guiding a laser to form a first step-weld with a laser beam,
    guiding the laser to form a second step weld with said laser beam,
    steering said laser beam back to said first step weld after said first step weld has solidified, wherein the laser beam is guided onto the first step weld with insufficient energy input to melt said first step-weld, and detecting the reflected signal data,
    comparing the detected reflected signal data with desired values,
    generating and recording in memory a violation signal each time the detected reflected signal data does not correspond with the desired values, and
    evaluating the quality of the laser weld seam on the basis of said violation signals.

15. A process for checking a laser weld seam, comprising:
    selecting materials to be welded and the process parameters of the laser welding process for forming a weld seam,
    determining the time after welding at which at least a thin skin has solidified on the weld seam and setting this as the earliest measurement start time for a characteristic interval,
    determining the minimal length of a time interval necessary in order to receive detectable signal data, and setting this as the minimal duration of the characteristic time interval,
    laser welding said materials to form a weld seam by a computer controlled process comprising:

receiving signals of optical and/or thermal type which are emitted out of the area of the seam in which at least a thin skin has solidified however the seam is still glowing, comparing the detected signal data with desired values, providing a violation signal each time the detected reflected signal data does not correspond with the desired values, and evaluating the laser weld seam on the basis of said violation signals, wherein only signals detected within the characteristic time interval are taken into consideration.

16. The process as in claim 15, wherein said signals are of the optical type.

17. The process as in claim 15, wherein said signals are of the thermal type.

* * * * *